(12) United States Patent
Bohner et al.

(10) Patent No.: US 11,234,760 B2
(45) Date of Patent: Feb. 1, 2022

(54) ELECTROSURGICAL DEVICE FOR CUTTING AND REMOVING TISSUE

(71) Applicant: MEDTRONIC ADVANCED ENERGY LLC, Minneapolis, MN (US)

(72) Inventors: Michelle Bohner, San Francisco, CA (US); Ralph I. McNall, Los Altos, CA (US); Hardev Kahlon, San Jose, CA (US)

(73) Assignee: Medtronic Advanced Energy LLC, Minneapolis, MN (US)

(*) Notice: Subject to any disclaimer, the term of this patent is extended or adjusted under 35 U.S.C. 154(b) by 592 days.

(21) Appl. No.: 13/796,817

(22) Filed: Mar. 12, 2013

(65) Prior Publication Data
US 2014/0100557 A1    Apr. 10, 2014

Related U.S. Application Data

(60) Provisional application No. 61/710,250, filed on Oct. 5, 2012.

(51) Int. Cl.
*A61B 18/14*        (2006.01)
*A61B 18/18*        (2006.01)
(Continued)

(52) U.S. Cl.
CPC ...... *A61B 18/1485* (2013.01); *A61B 18/1206* (2013.01); *A61B 18/18* (2013.01);
(Continued)

(58) Field of Classification Search
CPC ............ A61B 18/1206; A61B 18/1485; A61B 2018/00107; A61B 2018/00178; A61B 2018/00601; A61B 18/18
(Continued)

(56) References Cited

U.S. PATENT DOCUMENTS 2,888,928 A    6/1959  Seiger
3,682,130 A    8/1972  Jeffers
(Continued)

OTHER PUBLICATIONS

Berger et al., Histopathological Changes After Coblation Inferior Turbinate Reduction, Arch Otolaryngol Head Neck Surg. 2008;134(8):819-823.
(Continued)

*Primary Examiner* — Michael W Kahelin
*Assistant Examiner* — Pamela M. Bays
(74) *Attorney, Agent, or Firm* — Christopher & Weisberg, P.A.

(57) ABSTRACT

Electrosurgical devices including a shaft, a handle and a distal end portion. The distal end portion is formed of an electrically conductive material and includes an electrically insulating material covering a substantial portion of the distal end portion and leaving an exposed portion which acts as an active electrode for delivery of electrical energy to tissue. A conduit in the shaft extending to an opening in the distal end portion facilitates aspiration of tissue and may provide suction simultaneous with delivery of electrical energy. Systems include an electrosurgical device, a source of electrical energy and may optionally include a source of suction and/or a source of fluid delivery or irrigation.

10 Claims, 10 Drawing Sheets

(51) Int. Cl.
*A61B 18/12* (2006.01)
*A61B 18/00* (2006.01)

(52) U.S. Cl.
CPC .............. *A61B 2018/00101* (2013.01); *A61B 2018/00107* (2013.01); *A61B 2018/00178* (2013.01); *A61B 2018/00327* (2013.01); *A61B 2018/00601* (2013.01); *A61B 2218/002* (2013.01); *A61B 2218/007* (2013.01)

(58) Field of Classification Search
USPC .......................................................... 606/45
See application file for complete search history.

(56) References Cited

U.S. PATENT DOCUMENTS

| | | |
|---|---|---|
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,248,224 A | 2/1981 | Jones |
| 4,862,890 A * | 9/1989 | Stasz ................. A61B 18/1402 606/48 |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby et al. |
| 5,281,215 A | 1/1994 | Milder |
| 5,330,521 A | 7/1994 | Cohen |
| 5,334,181 A | 8/1994 | Rubinsky et al. |
| 5,336,220 A | 8/1994 | Ryan et al. |
| 5,364,395 A | 11/1994 | West |
| 5,383,874 A | 1/1995 | Jackson et al. |
| 5,385,148 A | 1/1995 | Lesh et al. |
| 5,395,312 A | 3/1995 | Desai |
| 5,401,272 A | 3/1995 | Perkins |
| 5,405,376 A | 4/1995 | Mulier et al. |
| 5,417,709 A | 5/1995 | Slater |
| 5,431,168 A | 7/1995 | Webster, Jr. |
| 5,431,649 A | 7/1995 | Mulier et al. |
| 5,441,503 A | 8/1995 | Considine et al. |
| 5,443,463 A | 8/1995 | Stern et al. |
| 5,445,638 A | 8/1995 | Rydell et al. |
| 5,460,629 A | 10/1995 | Shlain et al. |
| 5,490,819 A | 2/1996 | Nicholas et al. |
| 5,496,271 A | 3/1996 | Burton et al. |
| 5,505,700 A | 4/1996 | Leone |
| 5,540,562 A | 7/1996 | Giter |
| 5,542,196 A | 8/1996 | Hirsch et al. |
| 5,542,945 A | 8/1996 | Fritzsch |
| 5,556,397 A | 9/1996 | Long et al. |
| 5,562,702 A | 10/1996 | Huitema et al. |
| 5,569,243 A | 10/1996 | Kortenbach et al. |
| 5,573,424 A | 11/1996 | Poppe |
| 5,595,183 A | 1/1997 | Swanson et al. |
| 5,599,346 A | 2/1997 | Edwards et al. |
| 5,605,539 A | 2/1997 | Buelna et al. |
| 5,647,869 A | 7/1997 | Goble et al. |
| 5,681,294 A | 10/1997 | Osborne et al. |
| 5,688,267 A | 11/1997 | Panescu et al. |
| 5,697,536 A | 12/1997 | Eggers et al. |
| 5,697,882 A | 12/1997 | Eggers et al. |
| 5,713,942 A | 2/1998 | Stern |
| 5,733,280 A | 3/1998 | Avitall |
| 5,743,903 A | 4/1998 | Stern et al. |
| 5,766,167 A | 6/1998 | Eggers et al. |
| 5,797,905 A | 8/1998 | Fleischman et al. |
| 5,797,960 A | 8/1998 | Stevens et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,861,021 A | 1/1999 | Thome et al. |
| 5,873,855 A | 2/1999 | Eggers et al. |
| 5,879,348 A | 3/1999 | Owens et al. |
| 5,885,280 A * | 3/1999 | Nettekoven ............ A61B 18/14 439/332 |
| 5,891,142 A | 4/1999 | Eggers et al. |
| 5,895,355 A | 4/1999 | Schaer |
| 5,897,553 A | 4/1999 | Mulier |
| 5,904,681 A | 5/1999 | West, Jr. |
| 5,913,854 A | 6/1999 | Maguire et al. |
| 5,916,213 A | 6/1999 | Haissaguerre et al. |
| 5,921,982 A | 7/1999 | Lesh et al. |
| 5,925,045 A | 7/1999 | Reimels et al. |
| 5,927,284 A | 7/1999 | Borst et al. |
| 5,935,123 A | 8/1999 | Edwards et al. |
| 5,944,715 A | 8/1999 | Goble et al. |
| 5,928,191 A | 9/1999 | Houser et al. |
| 5,975,919 A | 9/1999 | Laufer |
| 5,971,980 A | 10/1999 | Sherman |
| 5,971,983 A | 10/1999 | Lesh |
| 5,980,516 A | 11/1999 | Mulier et al. |
| 5,989,248 A | 11/1999 | Tu et al. |
| 5,993,412 A | 11/1999 | Deily et al. |
| 6,004,316 A | 12/1999 | Laufer |
| 6,004,319 A | 12/1999 | Goble et al. |
| 6,010,500 A | 1/2000 | Sherman et al. |
| 6,012,457 A | 1/2000 | Lesh |
| 6,015,391 A | 1/2000 | Rishton et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,048,333 A | 4/2000 | Lennox et al. |
| 6,053,172 A | 4/2000 | Hovda et al. |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier |
| 6,109,268 A | 8/2000 | Thapliyal et al. |
| 6,110,170 A * | 8/2000 | Taylor .............. A61B 17/00008 606/41 |
| 6,117,101 A | 9/2000 | Diederich et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,190,381 B1 | 2/2001 | Olsen et al. |
| 6,193,715 B1 | 2/2001 | Wrublewski et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,293,957 B1 | 9/2001 | Peters et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |

(56) References Cited

U.S. PATENT DOCUMENTS

| | | |
|---|---|---|
| 6,328,736 B1 | 12/2001 | Mulier |
| 6,332,881 B1 | 12/2001 | Carver et al. |
| 6,355,032 B1 | 3/2002 | Hovda et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,461,357 B1 | 10/2002 | Sharkey et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,678 B2 | 12/2002 | Sherman |
| 6,488,680 B1 | 12/2002 | Francischelli |
| 6,502,575 B1 | 1/2003 | Jacobs et al. |
| 6,503,263 B2 | 1/2003 | Adams |
| 6,514,250 B1 | 2/2003 | Jahns |
| 6,527,767 B2 | 3/2003 | Wang et al. |
| 6,530,924 B1 * | 3/2003 | Ellman ............. A61B 18/1485 606/41 |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| 6,565,561 B1 | 5/2003 | Goble et al. |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,663,628 B2 | 12/2003 | Peters |
| 6,689,131 B2 | 2/2004 | McClurken |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,780,180 B1 | 8/2004 | Goble et al. |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,953,461 B2 | 10/2005 | Bloom et al. |
| 6,960,205 B2 | 11/2005 | Jahns |
| 6,962,589 B2 | 11/2005 | Mulier |
| 6,979,332 B2 | 12/2005 | Adams |
| 7,052,494 B2 | 5/2006 | Goble et al. |
| 7,070,596 B1 * | 7/2006 | Woloszko .......... A61B 18/1482 606/41 |
| 7,150,747 B1 | 12/2006 | McDonald et al. |
| 7,166,103 B2 | 1/2007 | Carmel et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,278,994 B2 | 10/2007 | Goble |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,442,191 B2 | 10/2008 | Hovda et al. |
| 7,537,595 B2 | 5/2009 | McClurken |
| 7,604,635 B2 | 10/2009 | Bloom et al. |
| 7,608,072 B2 | 10/2009 | Swanson |
| 7,645,277 B2 | 1/2010 | Bloom et al. |
| 7,651,494 B2 | 1/2010 | Bloom et al. |
| 7,691,050 B2 | 4/2010 | Gellman |
| 7,736,361 B2 | 6/2010 | Palanker |
| 7,785,337 B2 | 8/2010 | Adams et al. |
| 7,811,282 B2 | 10/2010 | McClurken |
| 7,815,634 B2 | 10/2010 | Bloom et al. |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | Bloom et al. |
| 8,105,323 B2 | 1/2012 | Buysse et al. |
| 8,172,828 B2 | 4/2012 | Chang et al. |
| 8,177,783 B2 | 5/2012 | Davison et al. |
| 8,216,233 B2 | 7/2012 | McClurken |
| 8,348,946 B2 | 1/2013 | McClurken |
| 8,361,068 B2 | 1/2013 | McClurken |
| 8,388,642 B2 | 3/2013 | Muni et al. |
| 8,632,533 B2 | 1/2014 | Greeley et al. |
| 8,632,537 B2 | 1/2014 | McNall, III et al. |
| 8,882,756 B2 | 11/2014 | Greeley et al. |
| 8,906,012 B2 | 12/2014 | Conley et al. |
| 8,920,417 B2 | 12/2014 | Conley et al. |
| 8,979,842 B2 | 3/2015 | McNall, III et al. |
| 2002/0049483 A1 | 4/2002 | Knowlton |
| 2002/0052600 A1 * | 5/2002 | Davison ............. A61B 18/1206 606/41 |
| 2002/0062131 A1 | 5/2002 | Gallo, Sr. |
| 2002/0082643 A1 | 6/2002 | Kammerer et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0176760 A1 * | 9/2004 | Qiu ................... A61B 18/1485 606/45 |

(56) References Cited

U.S. PATENT DOCUMENTS

| | | |
|---|---|---|
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2007/0049920 A1 | 3/2007 | Bloom et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0179495 A1 | 8/2007 | Mitchel et al. |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0207208 A1 | 8/2008 | Schutz |
| 2008/0262489 A1 | 10/2008 | Steinke |
| 2009/0118729 A1 | 5/2009 | Auth et al. |
| 2009/0264879 A1 | 10/2009 | Bloom et al. |
| 2009/0306655 A1 | 12/2009 | Stangenes |
| 2010/0100095 A1 | 4/2010 | Bloom et al. |
| 2010/0160906 A1 | 6/2010 | Jarrard |
| 2010/0168513 A1* | 7/2010 | Pless ................ A61B 1/00135 |
| | | 600/106 |
| 2010/0087812 A1 | 8/2010 | Davison et al. |
| 2010/0241178 A1 | 9/2010 | Tilson et al. |
| 2011/0028965 A1 | 2/2011 | McClurken |
| 2011/0054461 A1* | 3/2011 | Dickhans ............ A61B 18/148 |
| | | 606/33 |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0101496 A1 | 4/2012 | Davidson et al. |
| 2012/0116397 A1 | 5/2012 | Rencher et al. |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0179158 A1 | 7/2012 | Stierman |
| 2012/0184983 A1 | 7/2012 | Chang et al. |
| 2012/0191084 A1 | 7/2012 | Davison et al. |
| 2012/0253343 A1 | 10/2012 | McClurken et al. |
| 2013/0110108 A1 | 5/2013 | Davison et al. |

OTHER PUBLICATIONS

Lee et al, Comparative Study on the Long-Term Effectiveness Between Coblation-and Microdebrider-Assisted partial Turbinoplasty, Laryngoscope 116:May 2006 pp. 729-734.

Arthrocare PROcise EZ View Sinus Wand with integrated ablation, suction, and bipolar hemostasis (1 page) admitted prior art document.

* cited by examiner

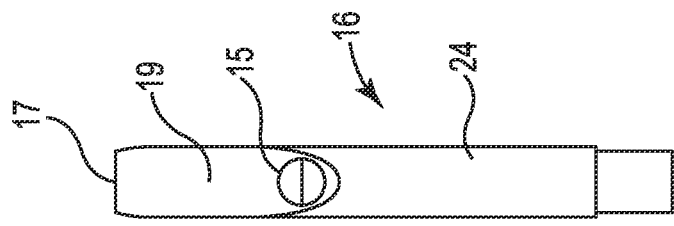
Fig. 9
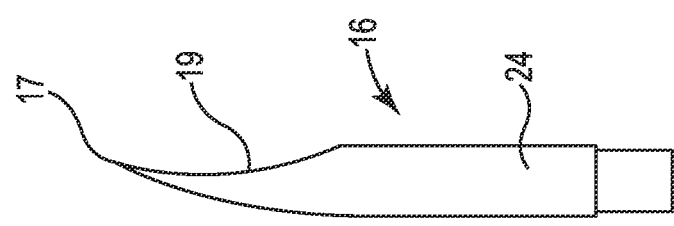 
Fig. 8          Fig. 10
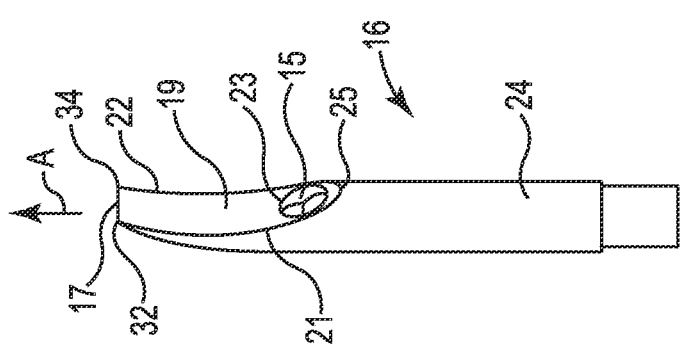
Fig. 7

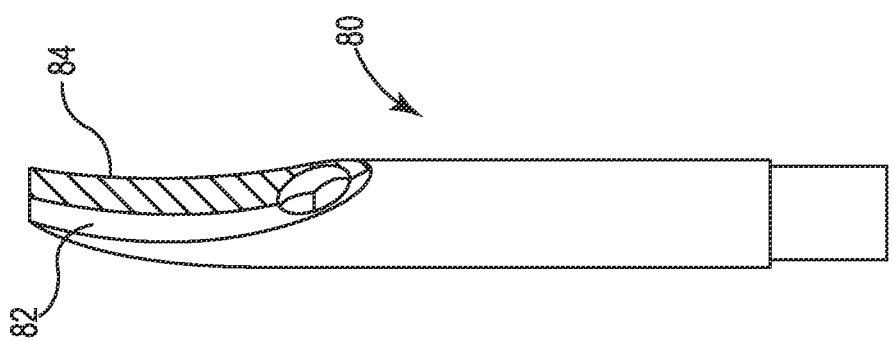

ELECTROSURGICAL DEVICE FOR CUTTING AND REMOVING TISSUE

CROSS REFERENCE TO RELATED APPLICATIONS

This application is related to and claims priority from U.S. provisional application 61/710,250, filed on Oct. 5, 2012, hereby incorporated by reference in its entirety.

BACKGROUND

The present disclosure relates generally to electrosurgical devices for resecting, cutting and/or removing tissue. More particularly, the disclosure relates to electrosurgical devices which integrate unique cutting surfaces with electrical energy and may additionally include aspiration and irrigation features which may work simultaneously with the cutting or resecting functions.

Devices of the present disclosure may be useful with a wide variety of electrosurgical procedures and may be particularly suitable for sinus and nasopharyngeal/laryngeal procedures such as those involving turbinate reduction, debulking of tongue tissue (e.g., midline glossectomies), lingual tonsillectomies, and/or polyp removal. Many of the procedures described may aid in managing or treating obstructive sleep apnea (OSA) or other breathing and/or snoring issues. Devices according to the disclosure may thus be constructed to cut or remove tissue or to debulk a region of interest and optionally may afford hemostasis and tissue shrinkage as well as irrigation of a targeted site and aspiration of blood, tissues or other fluids from the target site.

The human nasal septum divides the nasal cavity into right and left sides. The lateral nasal wall comprises inferior, middle, and supreme turbinate bones. In adults, the inferior turbinate is about the size of an index finger and the middle turbinate is about the size of the small finger. Turbinates are small, shelf-like structures composed of thin cancellous, spongy bone covered by mucous membranes. Turbinates function to move mucous via cilia on pseudostratified epithelia of nasal membrane which propel mucus from the nasal cavity and paranasal sinuses toward the nasopharynx where it can be swallowed. Cilia aid in protecting against infection and bacteria and are important for proper respiratory recognition and response. Turbinates regulate heat, humidify air, and pressurize and filter particulate from inhaled air. The turbinates also elevate and streamline air that flows through the nose and in this manner help maintain laminar flow. The turbinates protect the pharynx and larynx from direct insult of airflow and dryness.

The role of inferior turbinate pathology and the reduction of nasal airflow are well known. In short, the inferior turbinate of the sinus cavity may become enlarged or inflamed for a variety of reasons. Rhinitis is the inflammation of the mucous membranes of the nose. When the mucosa becomes inflamed, the blood vessels inside the membrane swell and expand, causing the inferior turbinates to become enlarged and obstruct the flow of air through the nose. Acute sinusitis (e.g. acute rhinosinusitis) causes the cavities around nasal passages (sinuses) to become inflamed and swollen. Sinusitis that lasts more than 12 weeks, or keeps coming back, is called chronic sinusitis. This inflammation obscures the patient's nasal airway, causing breathing difficulties. In cases where medicinal treatment fails, a preferred surgical treatment entails resecting submucous tissue of the inferior turbinate, thereby reducing the inferior turbinate size. Available techniques for turbinate reduction include total turbinectomy, partial turbinectomy (e.g. where the head of the inferior turbinate is resected), submucous resection or submucous turbinectomy, partial or complete turbinoplasty, cryotherapy, submucous electrosurgery, and laser turbinoplasty. Unfortunately, short-term and long-term complications such as scar formation, bleeding and atrophic rhinitis can occur with many of the above-listed procedures and often complications arise due to sacrifice of mucosa for access to the target site. See, e.g., Berger G, Ophir D, Pitaro K, Landsberg R. *Histopathological changes after Coblation® inferior turbinate reduction*, Arch Otolaryngol Head Neck Surg 2008; 134: 819-23; and Lee J Y, Lee J D. *Comparative study on the long-term effectiveness between Coblation-and microdebrider-assisted partial turbinoplasty*. Laryngoscope 2006; 116: 729-34.

It has been estimated that in the United States, there are about three hundred and sixty thousand turbinate reduction procedures per year conducted in an operating room setting and about fifteen thousand in-office turbinate reduction procedures per year. During such procedures, if too much turbinate structure is removed, the patient may suffer from Empty Nose Syndrome or Paradoxical Obstruction in which many of the beneficial functions provided by the turbinates may be lost. Other complications as described above may also occur. Sinus surgery is challenging due to its location to sensitive organs such as the eyes and brain, the relatively small size of the anatomy of interest to the surgeon, and the complexity of typical procedures. Despite challenges, devices have been developed which are particularly suitable for use in sinus surgery and more particularly may be useful in turbinate reduction surgery. See, e.g., Friedman N R. *Inferior turbinate reduction: an application for the microdebrider*, Oper Tech Otolaryngol 2005; 16:232-4 and Liu C-M, Tan C-D, Lee F-P, Lin K-N, Huang H-M. *Microdebrider-assisted versus radiofrequency-assisted inferior turbinoplasty* Laryngoscope 2009; 119:414-8. Debriders with mechanical cutting components are described in U.S. Pat. Nos. 5,685,838, 5,957,881 and 6,293,957. These devices are particularly successful for powered tissue cutting with sharp surfaces and removal during sinus surgery, but do not include any mechanism for sealing tissue to reduce the amount of bleeding from the procedure. Sealing tissue is desirable during surgical procedures especially if it can reduce blood loss or minimize the need for packing.

Surgical resecting instruments in which an elongate inner member is rotated or oscillated within an elongate outer tubular member has become well accepted in surgical procedures where access to the surgical site is gained via a narrow portal or passage. Typically, the outer tubular member includes a distal end defining a cutting port or window, and the inner member includes a distal end with a cutting tip for engaging and resecting bodily tissue via the cutting window. The cutting tip of the inner tubular member can have various configurations specific to the surgical procedure in question (e.g., resecting, cutting, shaving, abrading, etc.), with the cutting window being suitably configured to cooperate with the particular configuration of the cutting tip. Typically, the inner tubular member defines a lumen so that the loose tissue resulting from a cutting, resecting or abrading procedure can be aspirated from the target site. U.S. Pat. Nos. 6,503,263 and 7,785,337 describe a surgical microshaving instrument and a surgical micro-burring instrument respectively, each instrument having an inner tubular member maintained by an outer tubular member, and a distal tip configured to assist in tissue dissection. These devices may be particularly useful for inferior turbinate reduction procedures. The Medtronic Straightshot® M4

Microdebrider with Turbinate Blade is a system that works well in removing volume from a turbinate. As indicated above, the ideal procedure spares the mucosal lining, thereby promoting a quicker recovery and possibly decreasing the likelihood of excessive bleeding and the development of atrophic rhinitis. The blade of the Medtronic microdebrider (which has an elongated flat surface on one side that facilitates dissection) is sharp and is positioned at the anterior-inferior edge of the inferior turbinate. The blade is then bluntly inserted at a 45-degree angle until it touches the turbinate bone. The microdebrider may be set in oscillating mode at about 1000 cycles per second, and the blade is pushed posteriorly along the bone for about 2 cm. Once a pocket has been developed between the turbinate bone and submucosal layer, the blade is rotated to face the mucosa lining, and the submucosal layer is then resected. The Medtronic Straightshot® M4 Microdebrider uses sharp cutting surfaces to cut tissue, and suction to withdraw tissue. While turbinate reduction with the Medtronic microdebrider system is a simple and safe technique, some bleeding may occur. While the above-described devices may be useful and/or advantageous for several reasons, they do not include features dedicated to promoting hemostasis or bleeding management and therefore, nasal packing is often used.

Other electrosurgical devices for removing, cutting or otherwise treating tissue are disclosed, for example in U.S. Pat. Nos. 5,364,395, 6,565,561, 5,190,541 and 7,220,261. In addition, ArthroCare® Corporation sells a plurality of different wands suitable for turbinate reduction that utilize bipolar RF power. Specifically, the ArthroCare ReFlex Ultra® wands are used during sinus surgery and are available in both adult and pediatric sizes. ArthroCare® Coblation® devices are commonly used in office, out-patient procedures. Published U.S. Pat. Application No. 2012-0179158 also discloses a device for treating sinusitis. This device ablates tissue by use of multiple electrode wands, which are placed in the sinus to shrink tissue by the use of RF energy. An inflatable balloon to protect mucosal lining may also be used with the device.

The PK Diego powered dissector is commercially available from Gyms ACMI, (a group company of Olympus Corporation) of Bartlett, Tenn. This device utilizes two sharp cutting blade components that are moveable relative to each other, one of which acts as an electrode in a bipolar ablation system. The distal end portion of the device includes six layers to accomplish mechanical cutting and electrical coagulation. The dual use of one of the components as both a mechanical, oscillating cutting element and a portion of the bipolar system of the device is problematic for several reasons. First, the arrangement exposes the sharp mechanical cutting component to tissue just when hemostasis is sought. Second, the oscillation of the component may interfere with the electrode function of the component for providing hemostasis. It also requires more layers than necessary to construct a device with both sharp cutting surfaces and RF ablation features. Finally, this device has two separate modes of operation, either mechanical cutting or bipolar RF energy delivery. The device does not actively resect tissue while simultaneously providing hemostasis.

Despite the various devices described above, there remains a need for a device or system that affords hemostasis or effective blood management, is unlikely to harm the mucosal lining on the outer surface of the turbinate, allows a surgeon to orient the device to resect tissue away from bone, affords protection from unnecessary thermal damage due to over-aggressive electrotherapy, advantageously avoids oscillatory or rotatably movable members, and affords simultaneous delivery of suction and electrical energy to tissue to advantageously remove tissue or debris from a target site.

SUMMARY OF THE INVENTION

A system including an electrosurgical device for cutting tissue comprising a handle and a shaft having a longitudinal axis, a distal end portion with a distal edge having an exposed electrosurgical cutting surface substantially perpendicular to the longitudinal axis, an arcuate surface defined by lateral first and second arcuate edges, an electrical insulation layer coating substantially all of the distal end portion with the exception of at least the distal edge of the distal end portion such that the distal edge is exposed, a connector associating the electrosurgical device to an electrical energy source so that at least the distal edge comprises an electrode configured to deliver electrical energy to the tissue, and a source of electrical energy coupled to the connector. The device may include one or more conduits and one or more openings configured for fluid association with a source of suction and/or fluid such as saline. The device may also include one or more connectors adapted to associate the conduit(s) and opening(s) with the suction and/or fluid. The handle may include actuators for selectively actuating the suction, fluid and/or electrical energy.

An electrosurgical device for cutting tissue comprising a handle and a shaft having a longitudinal axis a distal end portion with a distal edge having an exposed electrosurgical cutting surface substantially perpendicular to the longitudinal axis, an arcuate surface defined by lateral first and second arcuate edges, an electrical insulation layer coating substantially all of the distal end portion with the exception of at least the distal edge of the distal end portion such that the distal edge is exposed, and a connector adapted to associate the electrosurgical device to an electrical energy source so that at least the distal edge comprises an electrode configured to deliver electrical energy to the tissue. The device may include one or more conduits and one or more openings configured for fluid association with a source of suction and/or fluid such as saline. The device may also include one or more connectors adapted to associate the conduit(s) and opening(s) with the suction and/or fluid. The handle may include actuators for selectively actuating the suction, fluid and/or electrical energy.

An electrosurgical device for cutting tissue comprising a handle and a shaft, the shaft having a longitudinal axis, a distal end portion including a distal edge having an exposed electrosurgical cutting surface that is substantially perpendicular to the longitudinal axis an arcuate surface extending proximally from the distal edge and terminating at a raised edge to define an arcuate ledge, the raised edge comprising an exposed electrosurgical cutting surface, first and second arcuate edges defining lateral edges of the arcuate ledge, an electrical insulation layer coating substantially all of the distal end portion except at least the distal edge of the distal end portion such that the distal edge is exposed, and an electrical connector adapted to associate the electrosurgical device to an electrical energy source so that at least the distal edge comprises an electrode configured to deliver electrical energy to the tissue. The device may include one or more conduits and one or more openings configured for fluid association with a source of suction and/or fluid such as saline. The device may also include one or more connectors adapted to associate the conduit(s) and opening(s) with the suction and/or fluid. The handle may include actuators for selectively actuating the suction, fluid and/or electrical energy.

An electrosurgical device comprising a handle and a shaft having a longitudinal axis and a conduit, a distal end portion comprising a sharpened distal edge having an exposed electrosurgical cutting surface that is substantially perpendicular to the longitudinal axis, an arcuate surface extending proximally from the distal edge, first and second arcuate edges defining lateral edges of the arcuate surface, an electrical insulation layer coating substantially all of the distal end portion with the exception of at least the distal edge of the distal end portion such that the distal edge is exposed, a connector adapted to associate the electrosurgical device to an electrical energy source comprising monopolar radio frequency energy such that at least the distal edge comprises an electrode configured to deliver electrical energy to the tissue, wherein the distal end portion comprises an opening on the arcuate surface in fluid communication with the conduit, and a connector adapted to associate the conduit and the opening with a suction source. The device may a conduit and an opening configured for fluid association with a source of fluid (e.g., saline). The device may also include a connector adapted to associate the fluid conduit and fluid opening with the fluid source. The handle may include actuators for selectively actuating the suction, fluid and/or electrical energy.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

In the drawings, where like numerals refer to like components throughout several views:

FIG. 7 is a perspective view of the distal end portion of FIGS. 3-6;

FIG. 8 is a side view of the distal end portion of FIGS. 3-7;

FIG. 9 is a top view of the distal end portion of FIGS. 3-8;

FIG. 10 is an end view of the distal end portion of FIGS. 3-9;

FIG. 18 is a perspective view of another embodiment of a distal end portion according to the present disclosure.

DETAILED DESCRIPTION

Figure 1:
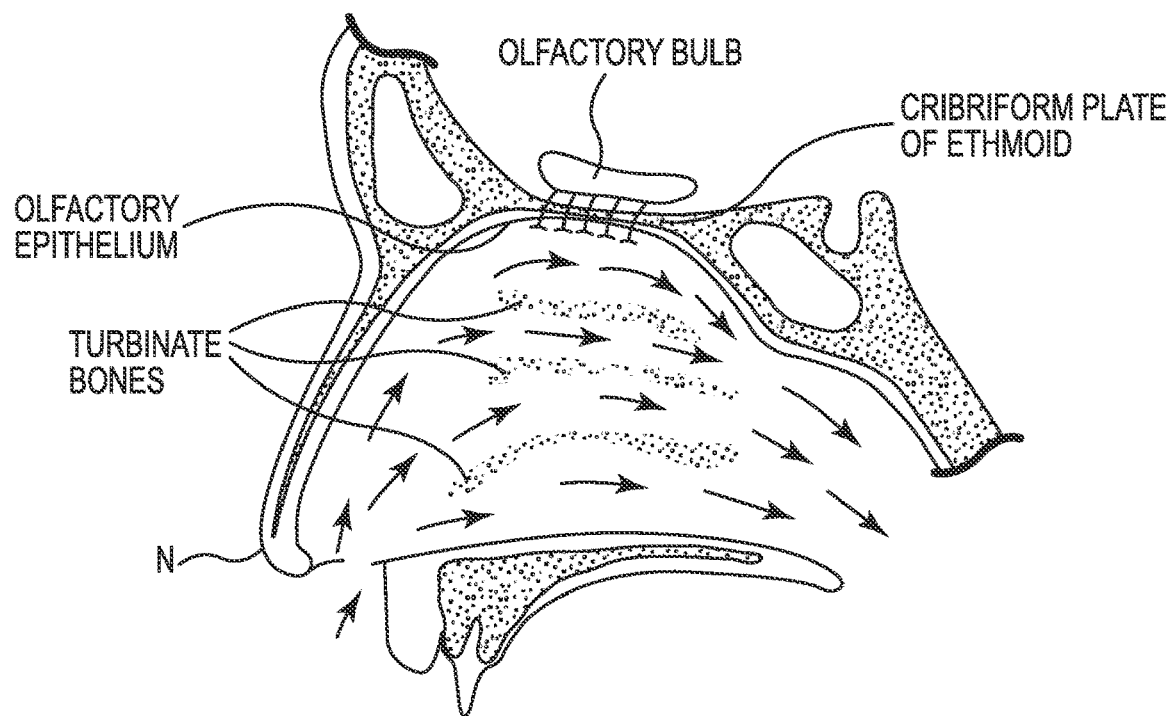
FIG. 1 is a schematic view of a human sinus showing the approximate location of turbinate bones.
Figure 2:
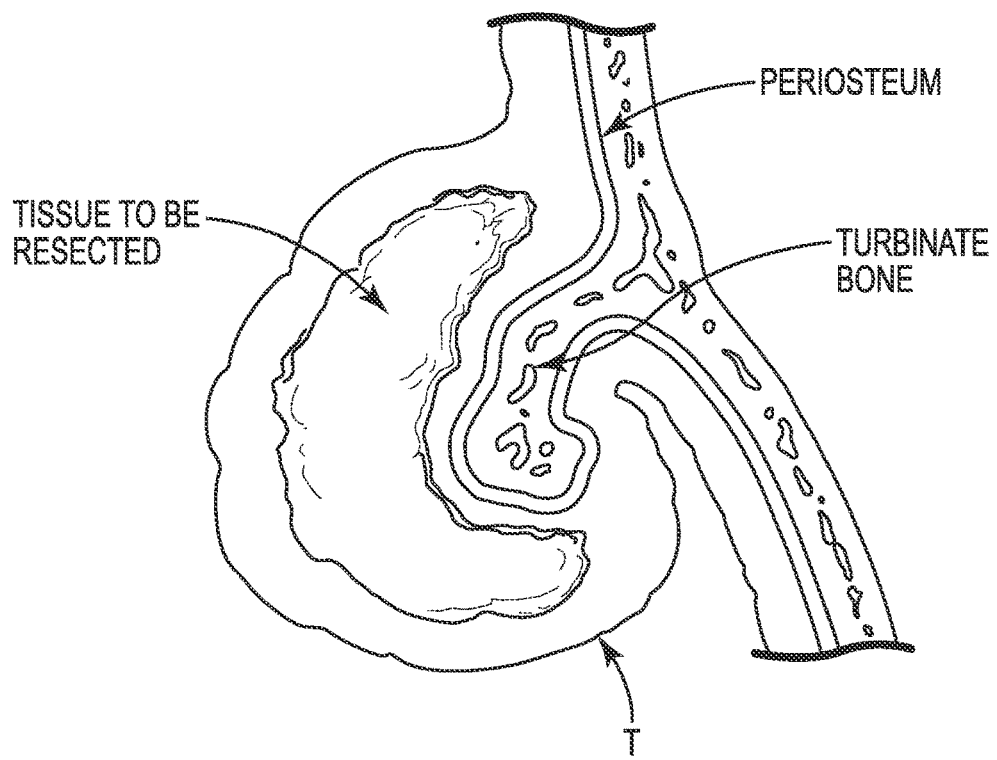
FIG. 2 is an enlarged view of a turbinate showing the approximate relative positions of turbinate bone and the periosteum as well as the location of tissue to be resected during turbinate reduction surgery.

FIG. 1 is a schematic illustration of the anatomy of a human sinus. The general relative locations of the turbinate bones, the olfactory epithelium, the olfactory bulb, the nose N and cribriform plate of the ethmoid are shown. FIG. 2 is an enlarged schematic representation of a turbinate T. The turbinate T includes periosteum, turbinate bone and tissue suitable to be resected/dissected and removed by devices of the present disclosure.

Figure 3:
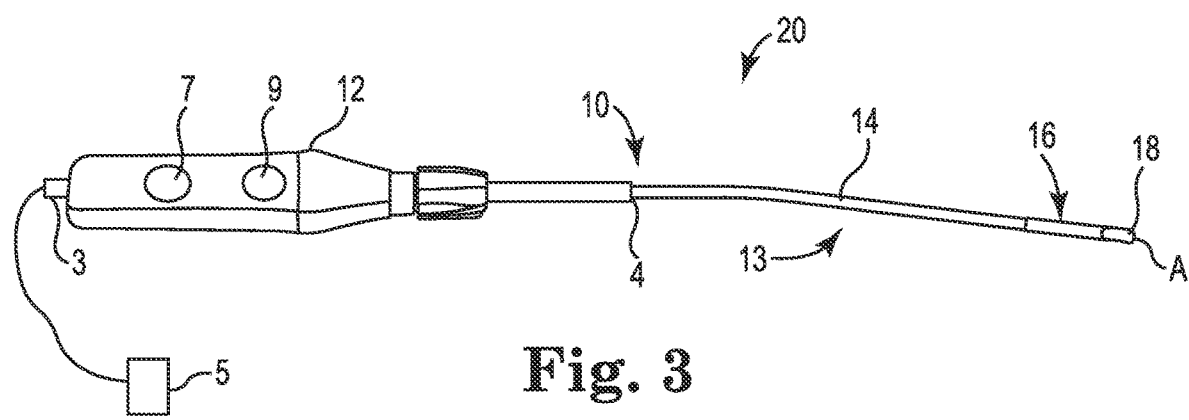
FIG. 3 is an photographic representation including a partial sketch of a system according to an aspect of the present disclosure showing an electrosurgical device including a handle and a shaft, and an source of electrical energy coupled to the device.
Figure 20:
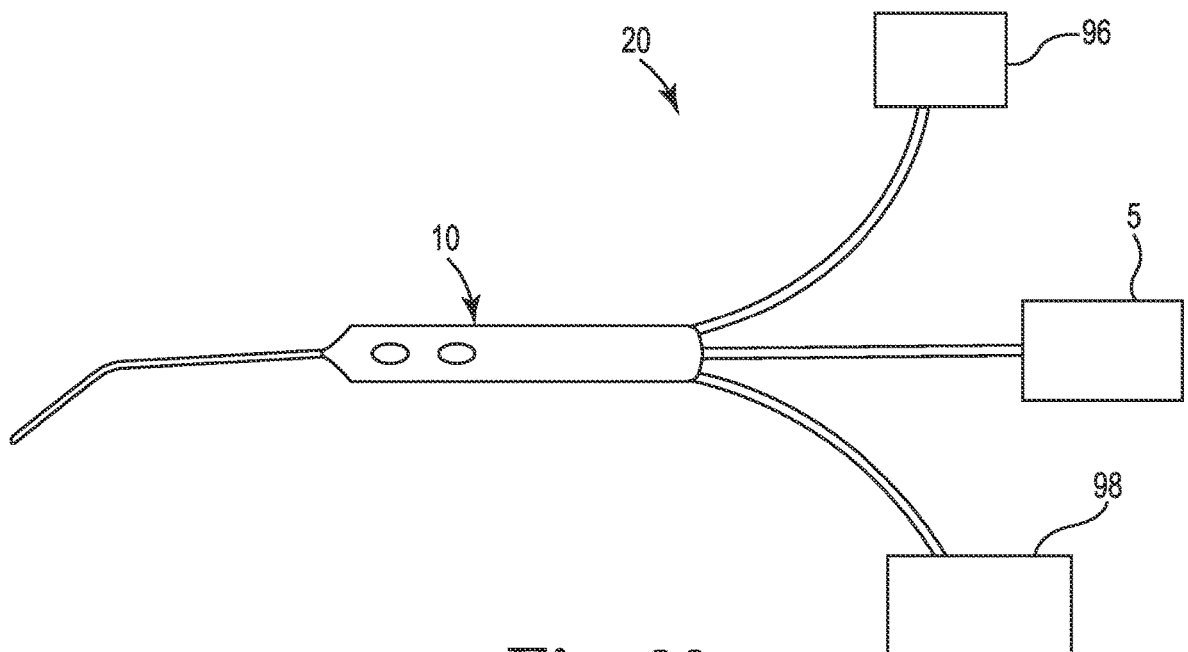
FIG. 20 is an illustration of a system according to the present disclosure.

FIGS. 3 and 20 show a system 20 according to aspects of the present disclosure.

System 20 includes a device 10 comprising a handle 12 and a shaft 13 having a longitudinal axis "A" where the shaft 13 includes a proximal shaft portion 14 and a distal end portion 16. Shaft 13 may include an internal conduit or passageway (not shown) configured for fluid communication with a source of suction 98 (FIG. 20), device 10 may therefore be capable of affording aspiration and removal of tissue (e.g., "t", FIGS. 17A-B) and other debris cut by distal end portion 16, described more fully herein below. Where shaft 13 includes a suction conduit, the suction conduit may extend from the proximal end 4 of shaft 13 to the distal end 18 of shaft 13 terminating at an opening 15 (FIG. 5) in distal end portion 16. The source of suction 98 may thus be connected to a suction source connection member (not shown) in, on or near handle 12 which may in turn be coupled to one of two actuators 7, 9 on handle 12 for selectively applying suction from the suction source 98, through the passageway, to the conduit opening 15 and thus to a target site. Notably and advantageously, suction or aspiration of tissue may be accomplished simultaneously with delivery of electrical energy to tissue or to a target site, as explained further herein below.

Figure 19:
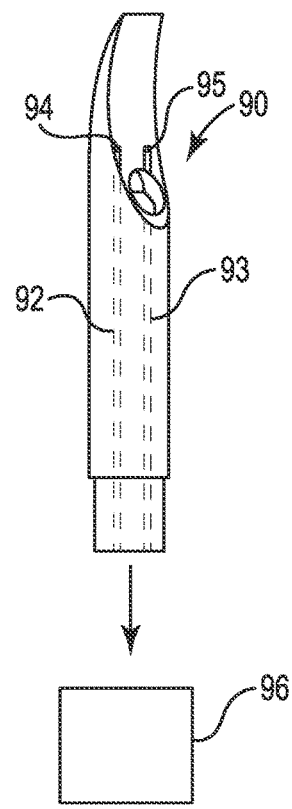
FIG. 19 is a perspective view of another embodiment of a distal end portion according to the present disclosure.

As depicted in FIGS. 19 and 20, system 20 may include a source of fluid 96 and additional conduits, ports or passageways may also be provided within shaft 13. For example, one or more irrigation or fluid delivery conduits may be provided in shaft 13 where the fluid delivery conduit or conduits are in fluid communication with the distal end portion (e.g., 16, 50, 80, 90) and a fluid delivery conduit opening or openings (e.g, 94, 95; FIG. 19) of a distal end portion (e.g., 90 etc.), which openings 94, 95 are fluidly associated with a source of fluid 96 (FIG. 19) such as saline or other liquids, described in further detail below. Additional actuators (not shown) for actuating a source of fluid may therefore be included on handle 12. As a further alternative, shaft 13 may comprise a substantially solid structure (i.e., no passageways or conduits terminating at a distal end portion opening).

Figure 4:
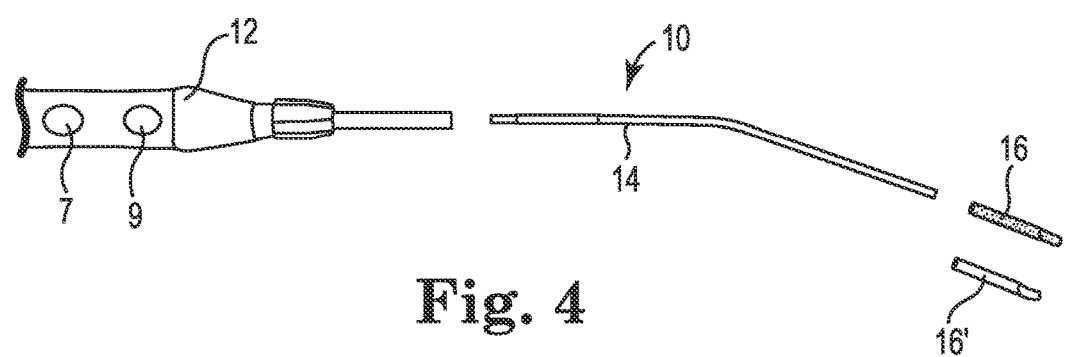
FIG. 4 is a photograph of the device of FIG. 3 in exploded or unassembled form where two distal end portions are shown, one with insulation and one without insulation.

Proximal shaft 14 is shown in a rigid, angled form, but may comprise other materials and shapes for example, semirigid or flexible and may be angled, straight or bendable. Regardless, proximal shaft 14 may be sized and configured for the specific procedure or targeted area intended. In addition, proximal shaft 14 and distal end portion 16 may comprise a unitary structure or may comprise separately formed members which are permanently or removably joined. Further, shaft 13 may be separable from handle 12 such that shaft 13 comprises a disposable portion of device 10. Likewise, proximal shaft 14, distal end portion 16 (i.e., shaft 13) and handle 12 may be separable as a unit from an electrical connector 3 such that the shaft 13 and handle 12 are a disposable portion of device 10. FIG. 4 depicts an exploded view of the electrosurgical device 10 of FIG. 3 where distal end portion 16 is shown apart from proximal shaft 14, which in turn is depicted in unassembled form such that proximal shaft 14 is separate from handle 12.

As depicted in FIG. 3, device 10 preferably connects to a source of electrical energy 5 via an electrical connector 3. The electrical energy source 5 may include monopolar or bipolar energy and may include radio frequency (RF) energy. As an example, the monopolar energy supplied by the PULSAR® generator to the PEAK PlasmaBlade™ System, available from Medtronic Advanced Energy, may be used. Where the electrical energy source 5 comprises monopolar energy, the assembly 10 would also include a patient ground pad (not shown). Selectively providing electrical energy to the device 10 may be accomplished via one of the actuators 7, 9 on handle 14. As indicated above, one of the actuators 7, 9 may be utilized to supply or remove suction while the other actuator 7, 9 may be utilized to supply or remove power to the distal end portion 16. Alternatively, the actuators 7, 9 can be replaced or disabled and one or more foot switches (not shown) may be utilized instead. The actuators 7, 9 (or foot switches) may be activated simultaneously to thereby simultaneously apply electrical energy and suction. Regardless of the type of actuator, electrical energy and aspiration may be accomplished simultaneously with the device 10. Providing suction concurrently with providing electrical energy to tissue advantageously allows for aspiration of debris and/or tissues cut by the electrodes (e.g., exposed edges 17, 21, 22 etc. described with reference to FIGS. 7-11)

Returning to FIG. 4, two distal end portions 16 and 16' are depicted. The distal end portions 16 and 16' are constructed from any suitable material, one non-limiting example being stainless steel. Distal end portion 16 depicts a distal end portion having an electrical insulation 24 while distal end portion 16' depicts a distal end portion without insulation. Proximal shaft 14 may also include an electrical insulation layer or coating which may be may be different from 16. Regardless, electrical insulation 24, and specifically the electrical insulation on distal end portion 16, may comprise a ceramic, glass or other suitable insulative coating or layer. Some examples of insulative coatings including glass and/or ceramic types are described in U.S. Pat. Nos. 6,135,998; 6,730,075; 7,357,802 and 7,736,361, and published U.S. Pat. No. 2008-0140066.

Another example of an electrically insulative coating is described in U.S. patent application Ser. No. 13/284,662, "Carbon Coated Electrode for Electrosurgery and its Method of Manufacture", incorporated by reference herein in its entirety. The electrical insulation 24 may act as both an electrical and a thermal insulation on the shaft 13 and in particular on the distal end portion 16 and may coat a substantial portion of the distal end portion 16 such that only an edge or edges of the distal end portion are exposed and are thereby active electrodes, described in further detail below. In this regard, electrical insulation 24 may coat or cover at least 90% of the surface area of distal end portion 16, at least 99% of the surface area of distal end portion 16 or may coat or cover at least 99.5% of the surface area of distal end portion 16. Stated another way, insulation 24 may coat substantially all of the distal end portion 16 with the exception of at least one edge (e.g., distal edge 17 described in further detail below) of distal end portion 16. The insulator material provided on shaft 14 may assume a variety of other electrical insulator forms, for example, the electrical insulator provided on shaft 14 can be an insulative sheath or shrink tubing covering portions of the shaft 14 and extending to a distal end of proximal shaft 14 or to a proximal portion of distal end portion 16. At least a portion of proximal shaft 14 does not include insulative material or coating such that the exposed portion is connectable to the electrical connector 3. Alternatively, another electrical connector such as an insulated wire or electrode trace may be provided along or within shaft 13 to connect distal end portion 16 with an electrical energy source 5.

Figure 5:
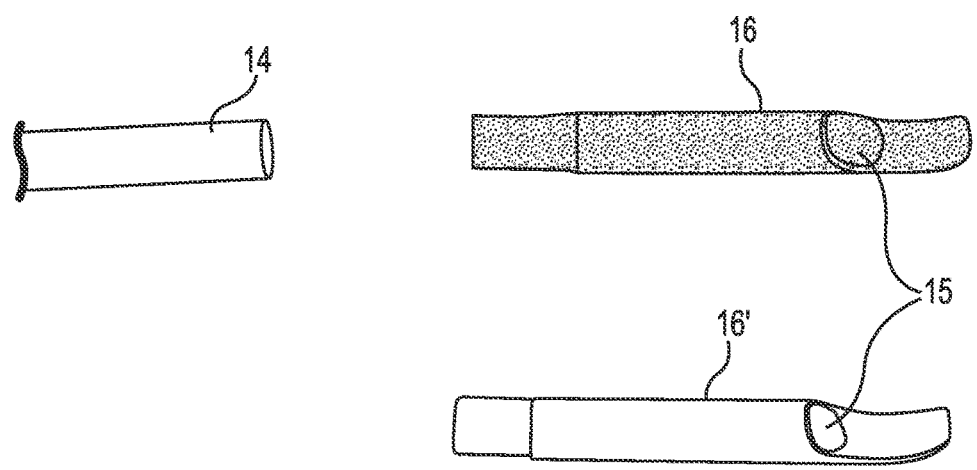
FIG. 5 is an enlarged photograph of a portion of the shaft and the two distal end portions of FIGS. 3-4.
Figure 6:
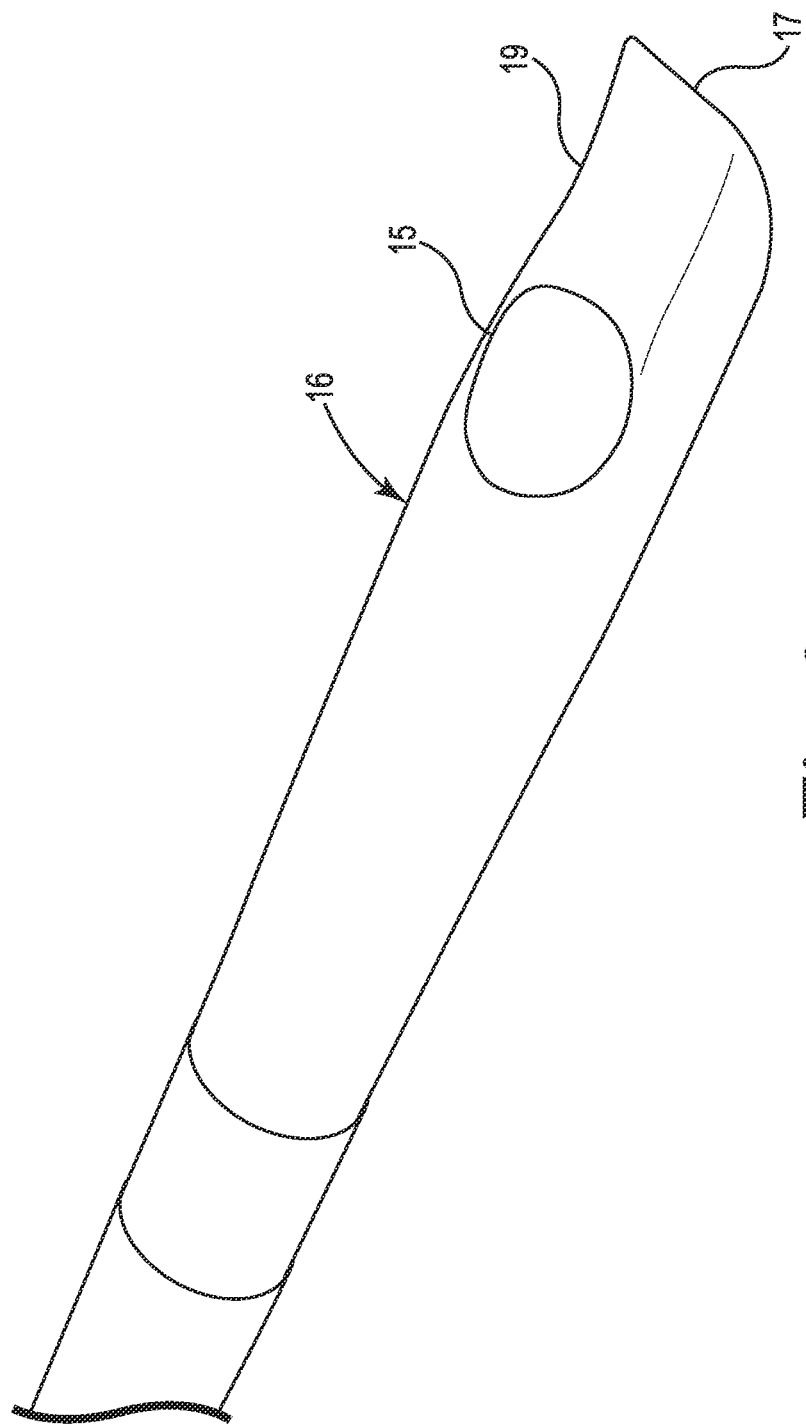
FIG. 6 is an enlarged perspective view of the distal end portion with insulation shown in FIGS. 3-5.

FIG. 5 depicts an insulated distal end portion 16 and non-insulated distal end portion 16' in enlarged form with a portion of proximal shaft 14 separated from distal end portion 16. FIG. 6 depicts a perspective view of enlarged distal end portion 16 showing conduit 15, an arcuate surface 19 and a distal edge 17. FIGS. 7-10 depict various views of distal end portion 16. It is to be understood that the features described with reference to distal end portion 16 may likewise be attributable to distal end portion 16', with the exception of the insulation 24. As seen most clearly in FIGS. 7-9, the distal end portion 16 includes conduit opening 15 defined by a conduit opening perimeter or edge 23. Conduit opening 15, as mentioned above, may be in fluid communication with a source of suction to provide suction at or near a region of cutting or near a targeted tissue treatment area (i.e., target site). Distal end portion 16 also includes distal edge 17 that may be substantially perpendicular to a longitudinal axis A of the distal end portion 16 (i.e., may comprise a straight as opposed to curved or rounded edge). FIG. 10 depicts an end view of distal end portion 16 showing perpendicular edge 17 and opening 15.

Optionally, the distal edge 17 may be sharp for piercing tissue and may be considered a thin distal edge. Advantageously, sharpened edge 17 may allow a surgeon to penetrate tissue with minimal damage to surrounding areas such as the mucosal tissue of a turbinate or other area of soft tissue or muscle. A sharpened distal edge 17 configured in this manner may also eliminate the need for an initial incision with a scalpel.

The distal end portion 16 also includes an arcuate surface 19 that forms a shovel or scoop-like surface, best seen in FIGS. 7 and 8. The scoop-like surface may act as an aid in the collection of tissue to be aspirated by the active suction. The arcuate surface 19 may in addition allow a user to angle the device toward the center of the turbinate where excess tissue is often present (see, e.g., FIG. 2). A first arcuate edge 21 and a second arcuate edge 22 define lateral edges of arcuate surface 19 and extend from a first arcuate edge distal end 32 and a second arcuate edge distal end 34 and meet at a proximal edge 25. Any of the edges, 17, 21, 22, 23 or 25 of distal end portion 16 may be coated with insulation or alternatively, may be exposed. Any of the edges not coated by the electrical insulation 24 (i.e., exposed edges) may thus be considered active electrodes such that exposed edges comprise exposed electrosurgical cutting surfaces (e.g., 17, 21, 22, 23 or 25) whereby when electrical energy from the electrical energy source 5 is generated, energy is transferred to the distal end portion 16 and is delivered to tissue through the electrosurgical cutting surface or surfaces. The small area of exposed electrode (i.e., edges) may be capable of generating plasma which may or may not be utilized during use of the device 10, depending on power settings and electrode arrangement. Because at least a portion of proximal shaft 14 is also free of insulation material 24 and is connected to the electrical energy source 5, electrical energy applied at the exposed portion of shaft 14 propagates to the exposed portion or portions (i.e., one or more exposed edge or edges 17, 21, 22, 23 or 25) of the distal end portion 16 for interaction with (e.g., dissecting/coagulating) contacted tissue. In other words, activation (e.g., via actuator 7, 9) of the electrical energy source 5 provides electrical energy at the exposed portion or portions (i.e., the active electrode edge or edges) of distal end portion 16. In this manner distal end portion 16, and in particular exposed edges of distal end portion 16, may provide optimal cutting of tissue that reduces blood loss, improves surgical visibility, reduces surgical times and reduces or eliminates char or undue damage to tissue, such as thermal necrosis. Tissue or other structures in contact with the shaft 13 at locations other than the exposed portions are not affected by the applied energy due to insulator or insulation 24.

Figure 11:
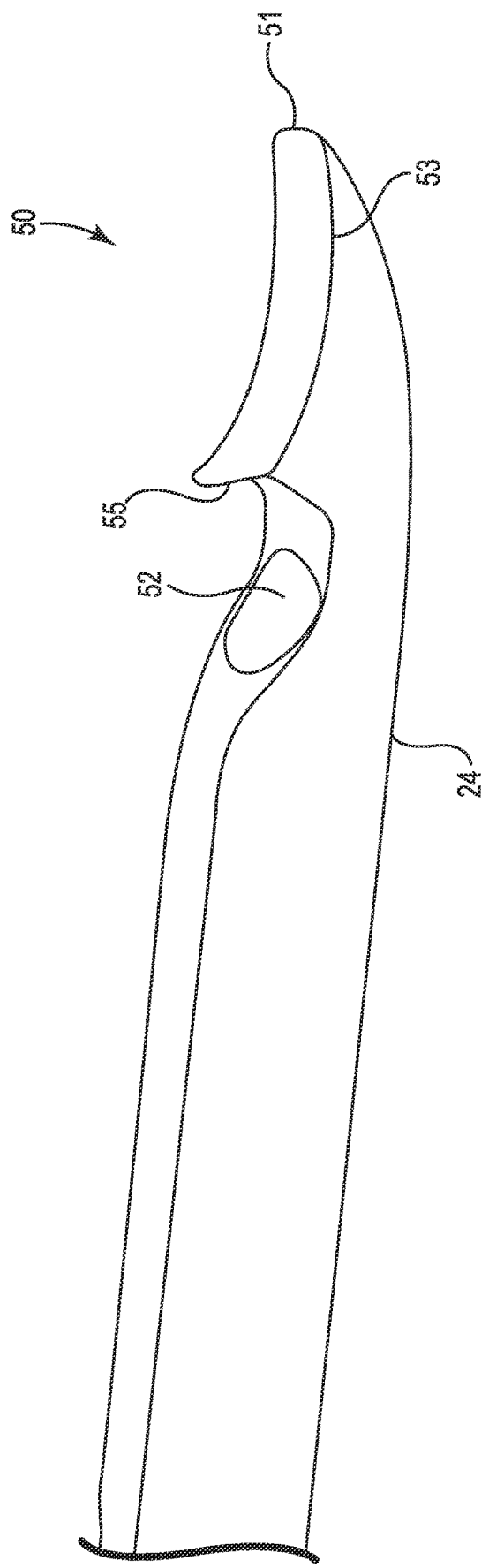
FIG. 11 is an enlarged side view of an alternative embodiment of a distal end portion according to the present disclosure.
Figure 12:
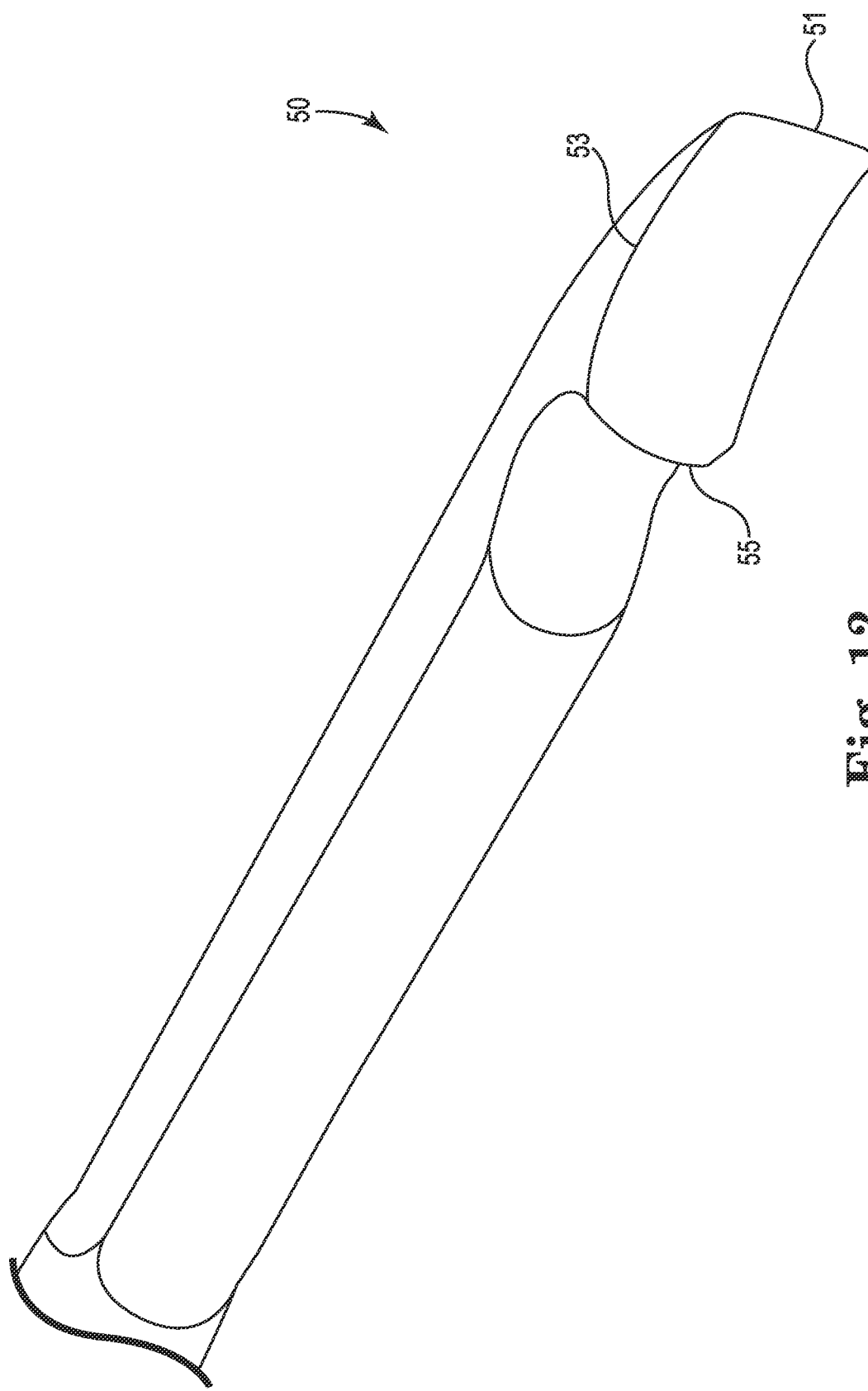
FIG. 12 is a perspective view of the of the distal end portion of FIG. 11.
Figure 15:
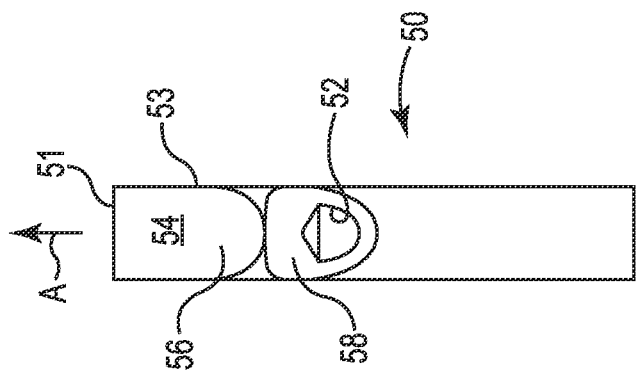
FIG. 15 is a top view of the distal end portion of FIGS. 11-12.
Figure 16:
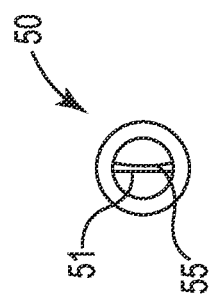
FIG. 16 is end view of the distal end portion of FIGS. 11-12.

FIGS. 11-17B show another embodiment of a distal end portion according to the disclosure. FIGS. 11 and 12 show two perspective views of distal end 50 having insulation 24 such as described above with respect to distal end portion 16. Distal end portion 50 also includes a distal edge 51 that may be configured similar to distal edge 17 of distal end portion 16 whereby distal edge 51 is substantially perpendicular to a longitudinal axis A of the distal end portion 50 (i.e., may comprise a straight as opposed to curved or rounded edge). FIG. 16 shows a top view of distal end portion 50 showing perpendicular edge 51. Optionally, the distal edge 51 may be sharp for piercing tissue and may be considered a thin distal edge such as described with reference to distal edge 17 of distal end portion 16.

Figure 14:
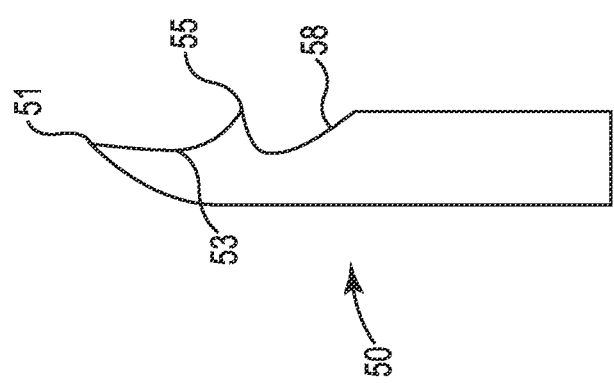
FIG. 14 is a side view of the distal end portion of FIGS. 11-12.
Figure 13:
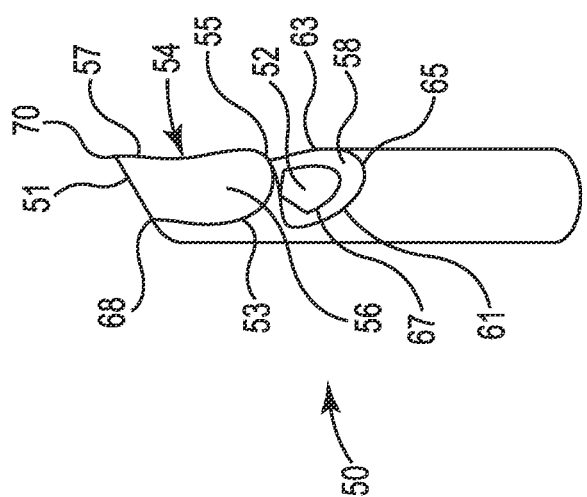
FIG. 13 is a perspective view of the distal end portion of FIGS. 11-12.

Distal end portion 50 also includes an arcuate surface 56 extending from distal edge 51, however, unlike arcuate surface 19 of distal end portion 16, arcuate surface 56 extends to a raised edge 55 to form an arcuate ledge 54 which forms a shovel or scoop-like surface. The arcuate surface 56 may in addition allow a user to angle the device toward the center of the turbinate such as described with reference to distal end portion 16. A first arcuate edge 53 and a second arcuate edge 57 define lateral edges of arcuate surface 56 and extend from a first arcuate edge distal end 68 and a second arcuate edge distal end 70 and meet at raised edge 55. Also, unlike distal end portion 16, distal end portion 50 may include a second arcuate surface 58 defined by a third arcuate edge 61 and a fourth arcuate edge 63 which extend from raised edge 55 to a proximal edge 65. As best seen in FIGS. 13 and 14, second arcuate surface includes a conduit opening 52 defined by a conduit opening perimeter or edge 67 (FIG. 13). Conduit opening 52, may thus be located proximal to arcuate surface 54 and may be in fluid communication with a source of suction to provide suction at or near a region of cutting or near a targeted tissue treatment area (i.e., target site).

Figure 17A:
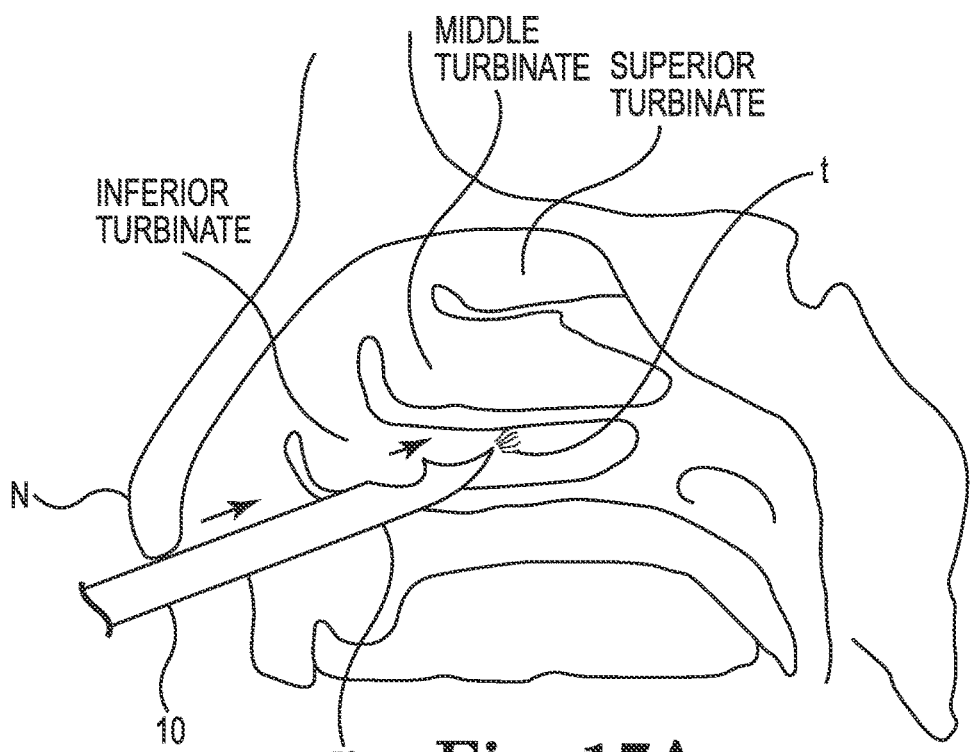
FIG. 17A is an illustration of an embodiment of a device according to the disclosure illustrating a device-tissue interaction where the device is moved in a first direction.
Figure 17B:
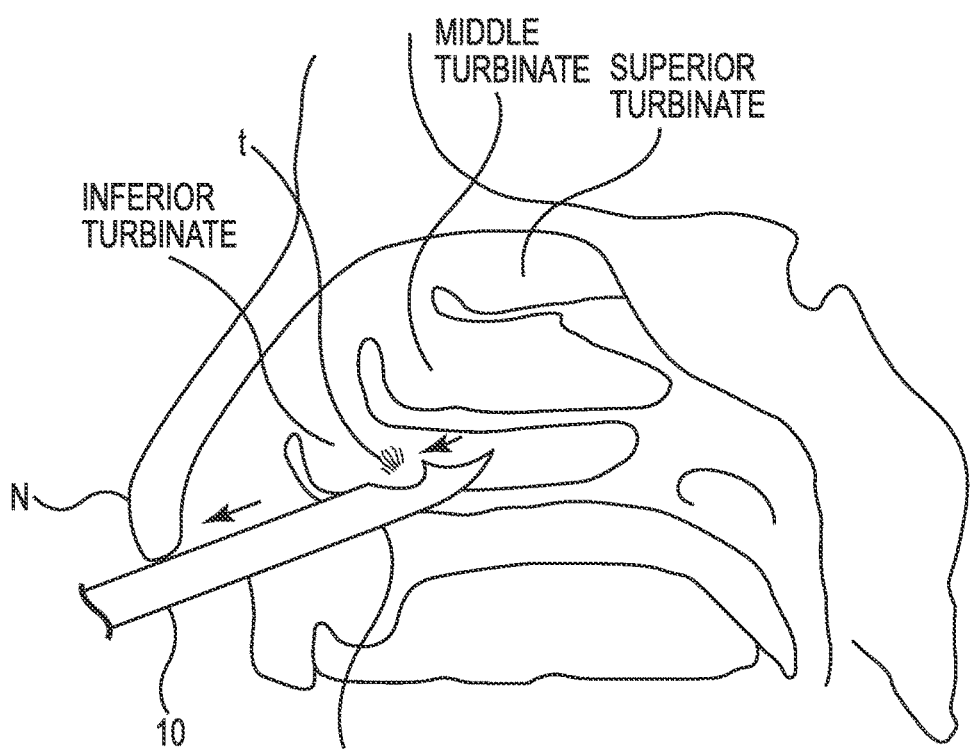
FIG. 17B is an illustration of an embodiment of a device according the present disclosure illustrating a device-tissue interaction where the device is moved in a second direction.

As with distal end portion 16, any of the edges, 51, 53, 55, 57, 61, 63, 65, and 67 of distal end portion 50 may be coated with insulation or alternatively, may be exposed. Any of the edges not coated by the electrical insulation 24 (i.e., exposed edges) may thus be considered active electrodes such that the exposed edges comprise exposed electrosurgical cutting surfaces whereby when electrical energy from the electrical energy source 5 is generated, energy is transferred to the distal end portion 50 and is delivered to tissue through the non-insulated portions or edges. Since edge 55 may be an electrically active edge, distal end portion 50 may cut and coagulate tissue when the distal end portion 50 (i.e., device 10) is moved both in a proximal and distal direction relative to the axis A making distal end portion 50 more aggressive than the device of FIGS. 3-10. FIG. 17A illustrates device 10 having distal end portion 50 moved or pushed in a distal or forward direction (i.e., away from the user) whereby tissue "t" is affected by distal edge 51. FIG. 17B illustrates device 10 having distal end portion 50 moved or pulled in a proximal or backward direction (i.e., toward the user) whereby tissue "t" is affected by raised edge 55.

Optionally, and as mentioned above, devices of the present disclosure may be designed for use with bipolar energy or a bipolar energy supply (e.g., 5 FIGS. 1, 20). For example, the transcollation sealing energy supplied by the Aquamantys® System (available from Medtronic Advanced Energy of Portsmouth, N.H.) may be used. U.S. Pat. Nos. 6,558,385; 6,702,810, 6,953,461; 7,115,139, 7,311,708; 7,537,595; 7,645,277 and 7,811,282 also describe bipolar ablation energy systems suitable for use with embodiments of the present disclosure. As an example, insulation and bare or exposed surfaces may be exploited to construct separate independent electrodes out of first and second exposed electrode surfaces (e.g., 55 and 51), other portions of a distal end portion may alternatively be exposed to form bipolar electrodes. One embodiment of a distal end portion 80 having a bipolar electrode arrangement is depicted in FIG. 18 where distal end portion 80 includes an active electrode 84 and a return electrode 84. As indicated above, several other bipolar electrode arrangements may also be provided and may likewise be provided on each of the distal end portions 16, 16', 50 etc. described herein.

In addition, as described above and depicted in FIGS. 19 and 20, system 20 may be configured for use with a source of fluid 96. One embodiment of a distal end portion 90 including fluid delivery conduits 92, 93 having fluid delivery conduit openings 94, 95 is shown in FIG. 19. Alternatively, only one fluid delivery conduit may be provided in distal end portion 90. Regardless, a fluid delivery conduit or conduits 92, 93 may be provided on any of the distal end portions (e.g., 16, 16', 50, 80) described herein and may be provided at various locations in or on shaft 14 and/or distal end portion 90. A fluid which may be particularly useful with the present embodiments is saline. In some embodiments, fluid delivery conduit 92, 93 may be configured to deliver saline through the conduit 92, 93 concurrent with delivery of electrical energy to provide controlled thermal energy to tissue to minimize charring and/or "sticking" of active electrode surfaces or edges (e.g., 17, 21, 22, 23 or 25 etc.).

Devices, systems and methods according to the present are suitable for otology procedures such as mastoidectomies and mastoidotomies; for nasopharyngeal and laryngeal procedures such as tonsillectomies, tracheal procedures, adenoidectomies, laryngeal lesion removal, and polypectomies; for sinus procedures such as polypectomies, septoplasties, removals of septal spurs, anstrostomies, frontal sinus trephination and irrigation, frontal sinus opening, endoscopic DCR, correction of deviated septums and transsphenoidal procedures; and for head and neck procedures such as soft tissue shaving, rhinoplasty and removal of fatty tissue in the maxillary and mandibular regions of the face. The electrosurgical cutting provided by the present invention affords efficient and effective cutting, dissection, removal and hemostatic sealing of tissue while minimizing char and bleeding. This is particularly desirable for sinus surgery which typically requires uncomfortable sinus packing just after cutting.

The complete disclosures of the patents, patent documents, and publications cited herein are incorporated by reference in their entireties as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An electrosurgical device for cutting tissue comprising:
a handle;
a shaft having a major longitudinal axis and defining an exterior surface;
the shaft including a distal end portion comprising a distal most edge having an exposed electrosurgical cutting surface that is substantially perpendicular to the longitudinal axis;
the distal end portion including a fluid delivery conduit extending therethrough;
a first concave surface extending proximally from the distal most edge along the major longitudinal axis;
first and second arcuate edges defining lateral edges of the first concave surface;
a second concave surface separate and distinct from the first concave surface, the second concave surface extending proximally from the first concave surface;
an electrical insulation layer coating substantially all of the distal end portion with the exception of at least the distal most edge of the distal end portion such that the distal most edge is exposed;
a first connector configured to associate the electrosurgical device to an electrical energy source so that at least the distal most edge comprises an electrode configured to deliver electrical energy to the tissue;
a second connector configured to associate the distal end portion with a suction source, the device being configured to deliver suction simultaneously with the delivery of electrical energy; and
a single opening in the distal end portion in fluid communication with the fluid delivery conduit, the opening being co-terminus with the fluid delivery conduit and with a proximal end of the second concave surface, the opening defining a diameter encompassing a majority of a maximum outer diameter of the distal end portion.

2. The electrosurgical device of claim 1, further including an electrical energy source coupled to the first connector whereby the device and the electrosurgical device comprise a system.

3. The system of claim 2, wherein the electrical energy source comprises monopolar radiofrequency energy.

4. The electrosurgical device of claim 1, wherein the electrical insulation layer coats at least 99% of the distal end portion.

5. The electrosurgical device of claim 1, wherein the shaft is configured for removable attachment to the handle.

6. The electrosurgical device of claim 1, wherein a proximal edge of the concave surface is not coated with the electrical insulation layer such that the proximal edge is exposed and comprise an electrode configured to deliver electrical energy to the tissue.

7. An electrosurgical device for cutting tissue comprising:
a handle;
a shaft having a major longitudinal axis and defining an exterior surface;
the shaft including a distal end portion comprising a distal most edge having an exposed electrosurgical cutting surface that is substantially perpendicular to the longitudinal axis, the distal end portion including a fluid delivery conduit extending therethrough;
a first concave surface extending proximally from the distal most edge along the major longitudinal axis and terminating at a raised edge to define an arcuate ledge, the raised edge comprising an exposed electrosurgical cutting surface;
first and second arcuate edges defining lateral edges of the arcuate ledge of the first concave surface;
a second concave surface separate and distinct from the first concave surface, the second concave surface extending proximally from the first concave surface;
an electrical insulation layer coating substantially all of the distal end portion except at least the distal most edge of the distal end portion such that the distal most edge is exposed;
an electrical connector configured to associate the electrosurgical device to an electrical energy source so that at least the distal most edge comprises an electrode configured to deliver electrical energy to the tissue; and
a single opening in the distal end portion in fluid communication with the fluid delivery conduit, the opening being co-terminus with the fluid delivery conduit and with a proximal end of the second concave surface, the opening defining a diameter encompassing a majority of a maximum outer diameter of the distal end portion.

8. The electrosurgical device of claim 7, wherein the fluid delivery conduit is configured to fluidly associate the distal end portion with a suction source.

9. The electrosurgical device of claim 7, wherein the electrical energy source comprises monopolar radiofrequency energy.

10. An electrosurgical device comprising:
a handle;
a fixed shaft having a major longitudinal axis, a conduit, and defining an exterior surface;
the shaft defining a distal end portion comprising a sharpened distal edge having an exposed electrosurgical cutting surface that is substantially perpendicular to the longitudinal axis,
a first concave surface extending proximally from the distal edge along the major longitudinal axis, the distal edge not extending beyond an outer lateral diameter of the shaft;

first and second arcuate edges defining lateral edges of the first concave surface;

a second concave surface separate and distinct from the first concave surface, the second concave surface extending proximally from the first concave surface;

an electrical insulation layer coating substantially all of the distal end portion with the exception of at least the distal edge of the distal end portion such that the distal edge is exposed;

a first connector configured to associate the electrosurgical device to an electrical energy source comprising monopolar radio frequency energy such that at least the distal edge comprises an electrode configured to deliver electrical energy to an area of tissue;

the distal end portion comprises a single opening in fluid communication with the conduit, the opening being co-terminus with the conduit and with a proximal end of the second concave surface, the opening defining a diameter encompassing a majority of a maximum outer diameter of the distal end portion and being coplanar with the second concave surface; and a second connector configured to associate the conduit and the opening with a suction source.

* * * * *